United States Patent [19]

Wagner

[11] 4,375,696

[45] Mar. 1, 1983

[54] METHOD OF DETERMINING THE BODY CONTOUR FOR THE RECONSTRUCTION OF THE ABSORPTION OF RADIATION IN A FLAT ZONE OF A BODY

[76] Inventor: Wolfgang Wagner, Bookholtstwiete 11, 2000 Hamburg 63, Fed. Rep. of Germany

[21] Appl. No.: 111,580

[22] Filed: Jan. 14, 1980

[30] Foreign Application Priority Data

Jan. 15, 1979 [DE] Fed. Rep. of Germany ....... 2901406

[51] Int. Cl.³ .............................................. G03B 41/16
[52] U.S. Cl. ...................................... 378/20; 364/414; 378/901
[58] Field of Search .................................... 250/445 T

[56] References Cited

FOREIGN PATENT DOCUMENTS 2551584 5/1977 Fed. Rep. of Germany ... 250/445 T

*Primary Examiner*—Craig E. Church
*Attorney, Agent, or Firm*—Jack E. Haken

[57] ABSTRACT

The invention relates to a method of determining the contour of a body positioned on an examination table in order to reconstruct an absorption distribution of a radiation in a flat examination zone of the body. During a first step, the contour zone of the body situated opposite the examination table is determined, for example, by means of an optical auxiliary radiation source, so-termed first contour points thus being derived. Starting from these first contour points, so-termed absorption lengths are plotted in the direction of the body on the beam paths extending through the first contour points and the examination zone in order to approximate the contour points of the body facing the examination table. The absorption lengths are the quotients of an absorption value associated with a beam path and a predetermined mean absorption coefficient.

4 Claims, 4 Drawing Figures

METHOD OF DETERMINING THE BODY CONTOUR FOR THE RECONSTRUCTION OF THE ABSORPTION OF RADIATION IN A FLAT ZONE OF A BODY

The invention relates to a method of determining the contour of a body positioned on an examination table for the reconstruction of an absorption distribution of radiation in a flat examination zone of the body, the examination zone which is situated within a positioning zone being completely irradiated by measuring beams from a radiation source in different directions which are situated in the plane of examination, for each direction along a number of beam paths, in order to determine absorption values, the positioning zone being irradiated by auxiliary radiation which is situated in the plane of examination, which is substantially or completely absorbed by the body, and which passes through at least a zone which directly adjoins the examination zone and which is tangent to the positioning zone, said auxiliary radiation being measured by means of auxiliary detectors in order to determine the position of auxiliary measuring beams which are tangent to the body, said positions being used to determine contour points of the body wherefrom the absorption distribution is reconstructed in conjunction with the absorption values.

A method of this kind is already known from the publication "Reconstruction from truncated scan data", by W. Wagner, published in MEDITA, special issue I/78. This method enables the reconstruction of the absorption distribution of radiation, for example, X-radiation, in an examination zone (for example, of a human body) which is situated in the irradiated plane (examination plane). The examination zone may completely or partly enclose the irradiated part of the body; in the latter case, for example, only separate organs of the body are examined. This means that the examination zone has a diameter which is substantially smaller than the positioning zone for the body in the plane. Contrary to the examination zone, the part of the body situated outside the examination zone is not completely irradiated in each direction, so that the radiation load for the body is limited.

In order to prevent errors in the reconstructed absorption distribution of the examination zone, fictitious absorption data ($\overline{Q}(p, \theta)$) must be determined for the parts of the body which are situated outside the examination zone and which are not completely irradiated by the measuring beams; these fictitious absorption data should correspond with some accuracy to the actual absorption data ($Q(p, \theta)$). However, for this purpose it is necessary to know at least the body contour. As described in said publication, this contour is measured by means of auxiliary radiation sources which emit auxiliary radiation which is substantially or completely absorbed by the body and which is situated in the plane. The auxiliary radiation is emitted directly in the zone adjoining the examination zone and is tangent to the boundary of the positioning zone. Part of the auxiliary radiation does not pass through the body and is incident on an array of auxiliary detectors which are situated in the plane and by means of which the distance between the auxiliary measuring beams tangent to the body and the examination zone is determined. By rotation of the assembly formed by the auxiliary radiation sources and the auxiliary detectors around the body, auxiliary measuring beams which are tangent to the body are produced in a large number of different directions. The contour of the body is then at least approximately described by the tangent auxiliary measuring beams.

The fictitious absorption data required for reconstruction of the absorption distribution in the examination zone are determined so that for each direction the zones of the body which are situated outside the examination zone and which are not irradiated by the measuring beams are subdivided into strips which extend in at least approximately the same direction as the measuring beams and which have substantially the same width as the beam paths followed by the mesuring beams. The length of the strip is limited by the body contour. To each strip there is assigned a predetermined absorption coefficient which is defined per unit of length and which at least approximates the mean body absorption coefficient. By multiplication of the preselected absorption coefficient by an associated strip length, absorption data are determined which are assigned to the relevant strip.

Using these absorption data, which are treated further as if they had been obtained by means of a measurement, and using the absorption values, the absorption distribution is reconstructed with a radiation load for the body which is substantially smaller.

For using the hereinbefore described method, however, the examination table may not intersect the positioning zone in order to allow unobstructed passage of the auxiliary radiation. However, customarily examination tables are used which over their entire length consist of a material which does not allow passage of the auxiliary radiation (light), for example, an (impermeable) synthetic material, so that only part of the body contour can be determined when this method is used.

Therefore, it is an object of the invention to provide a method which enables determination of the complete contour of a body positioned on a continuous examination table which is impermeable to the auxiliary radiation.

To this end, the method in accordance with the invention is characterized in that for the determination of first contour points of the body use is made of auxiliary measuring beams which are tangent to the body, on each beam path which extends through one of the first contour points of the body and through the examination zone there being determined a further contour point, a distance between said further contour point and the first contour point in the direction of the body having a value which equals a quotient ($L(p, \theta)$) of an absorption value ($Q(p, \theta)$) associated with the beam path and a predetermined, mean absorption coefficient ($\overline{\mu}$), p being a distance between a centre of the examination zone and a beam path, and $\theta$ being an angular position of the radiation source with respect to the centre of the examination zone.

When the method in accordance with the invention is used for an examination device comprising an "impermeable" examination table, the auxiliary measuring beams which are not tangent to the examination table measure only parts of the body contour, i.e. the section of the body contour which is situated opposite the examination table. To this end, for a given angle $\phi$ which is defined with respect to a coordinate axis of a system of coordinates whose origin coincides with the centre of the examination zone, vectors are defined which start from the origin and which point towards the contour section of the body whereto the auxiliary measuring beams are tangent, each of said vectors intersecting several auxiliary measuring beams. The length (the end) of the vectors is determined by the position of the point of intersection which is situated nearest to the origin. This will be elaborated at a later stage. The ends of the vectors represent a first group of contour points of the body. Starting from the first group of contour points thus measured, on all beam paths extending through the first contour points and through the examination zone there is plotted, in the direction of the body, a length which, for each path defined by (p, $\theta$), is defined by the quotient L(p, $\theta$), so that a further group of contour points is obtained which is situated approximately opposite the first group of contour points. The body contour is almost completely defined by the first group and the further group of contour points.

In a further version of the method in accordance with the invention, on each beam path extending through the further group of contour points thus determined there is each time defined, proceeding from the further contour points in the direction of the body, an additional contour point, the distance between said additional contour point and said further contour point being determined by a value which corresponds to the quotient L(p, $\theta$) of the absorption value Q(p, $\theta$) associated with each beam path and the predetermined, mean absorption coefficient $\overline{\mu}$.

Through each further contour point there also extend a large number of beam paths which are situated in the plane and on which a length is plotted in the direction of the body which corresponds to a quotient L(p, $\theta$) in order to obtain additional contour points. The number of contour points which at least approximately describe the body contour is thus substantially increased.

In a further version of the method is accordance with the invention, several vectors A(r, $\theta$) which start from the centre of the examination zone and which reach as far as the contour points are averaged in a predetermined angular zone in order to define a corrected contour point. As a result, the contour of the body is more accurately determined. The measured contour points are to be understood to mean the first, the further and the additional contour points.

The invention will be described in detail hereinafter with reference to the accompanying diagrammatic drawing.

Figure 1:
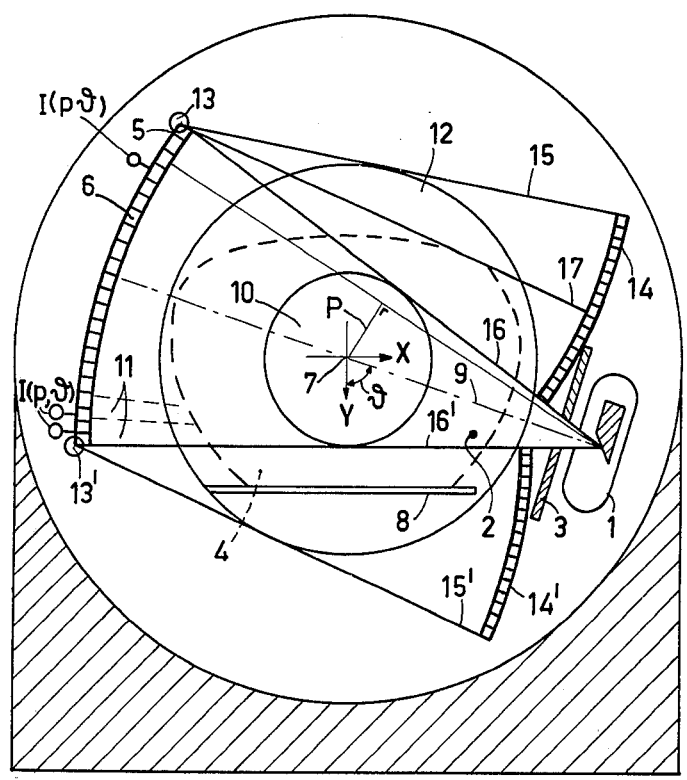
FIG. 1 is a sectional view of an X-ray tomography apparatus.

FIG. 1 is a diagrammatic sectional view of an X-ray tomography apparatus, comprising a radiation source 1 for emitting a fan-shaped X-ray beam 2 which extends in the plane of the drawing, which encloses the plane of examination and which is stopped by means of a lead aperture 3. The X-ray beam 2 irradiates a body 4 to be examined and is incident on an array of detectors 5 which consists of indidual radiation detectors 6 which are adjacently arranged in the plane of examination. The system formed by the radation source 1 and the detector array 5 is rotatable around a central axis 7 which extends perpendicularly to the plane of examination, the position of the system with respect to an orthogonal system of coordinates X, Y being denoted by an angle of rotation $\theta$ which is enclosed by the central ray 9 (between the source 1 and the centre of the detector array 5) of the fan-shaped radiation beam 2 and the Y-axis. The origin of the system of coordinates X, Y wherethrough the central axis 7 extends is at the same time the centre of the examination zone 10 of the X-ray tomography apparatus. This is the zone in the plane of examination which is completely irradiated by measuring beams extending along beam paths 11 at any angle of rotation $\theta$, the width of the beam paths 11 being determined by the width of the detectors 6. The position of a beam path is given by the distance P from the centre of the examination zone 10.

For the positioning of the body 4 to be examined (denoted by broken lines) in a positioning zone 12 which concentrically surrounds the examination zone 10, use is made of an examination table 8 which is adjustable perpendicularly to the plane of examination. The mechanical supporting system for this table has been omitted for the sake of simplicity.

By changing the position of the body 4 within the positioning zone 12, it can be achieved that the examination zone 10, whose dimensions can be changed by adjustment of the aperture 3, encloses different zones within the body 4 to be examined.

The body 4, however, may not cross the boundary of the positioning zone 12.

There are also provided optical auxiliary radiation sources 13, 13', which are situated at the ends of the detector array 5 and which emit two auxiliary radiation beams, situated in the examination plane and having extreme rays 15, 15' and 16, 16', in the direction of two auxiliary detector devices 14, 14', which consist of several separate detectors. The auxiliary detector devices 14, 14' which, like the auxiliary radiation sources 13, 13', rotate with the detector system, are arranged adjacent the radiation source 1 so that they can detect the extreme rays 16, 16' which also describe the boundary of the X-ray beam 2, and the extreme rays 15, 15' which are tangent to the positioning zone 12. As a result, the installation has a compact construction. For example, when an auxiliary measuring beam 17 is tangent to the contour of the body 4, the auxiliary detectors of the auxiliary detector device 14 between the auxiliary measuring beam 17 and the radiation source 1, will not be exposed to radiation so that they will not generate a signal, whilst the detectors of the auxiliary detector device 14 which are situated on the other side of the auxiliary measuring beam 17 receive radiation and supply an electronic unit (not shown) with an electrical signal. The position $P_t$ ($\theta$) of an auxiliary measuring beam 17 which is tangent to the body 4 can thus be readily determined. By rotation of the radiation source/detector device assembly around the central axis 7, for each angle $\theta$ auxiliary measuring beams 17 are determined; however, only the beams which are tangent to the body 4 but not to the examination table 8 are evaluated. For this purpose, the coordinates of the auxiliary measuring beams 17 which are tangent to the examination table 8 are derived in advance from the position of the examination table, so that an unambiguous determination of the auxiliary measuring beams 17 which are and which are not tangent to the table 8 is ensured.

Obviously, the tomography apparatus may alternatively comprise a single auxiliary radiation source 13 and an associated auxiliary detector device 14 which is oppositely arranged, if for a rotation of the scanning apparatus through less than 360° it is ensured that the auxiliary measuring beams 17 always scan the side of the body 4 which is remote from the examination table 8. The auxiliary radiation sources 13, 13' may be, for example, luminescent diodes emitting visible light or laser diodes emitting infrared radiation. Preferably, a common light source is coupled to two optical fibres, the ends of which are arranged in the positions at 13 and 13' as near as possible to the extreme rays 16, 16'. The auxiliary radiation sources and the auxiliary detector devices can be rotated around an axis 7, together with the radiation source 1 and the detector device 2. They may be rigidly connected to the measuring device consisting of the radiation source 1 and the detector device 5. If the radiation generated by the auxiliary radiation sources is modulated, for example, amplitude modulated, frequency modulated or pulse modulated, the measurement of the auxiliary radiation is less susceptible to ambient light and noise.

It is alternatively possible to use ultrasonic sound as the auxiliary radiation. In accordance with the so-called "phased array" principle, more than one ultrasonic transmitter can then be used, these transmitters being simultaneously activated with the same frequency, but in a different phase, the phase or the phase differences between the individual ultrasonic transmitters being continuously changed by means of suitable delay circuits. Thus, the direction of the ultrasonic beam is continuously changed, so that it scans the surface of the associated ultrasonic receiver on the other side of the examination zone.

Figure 2:
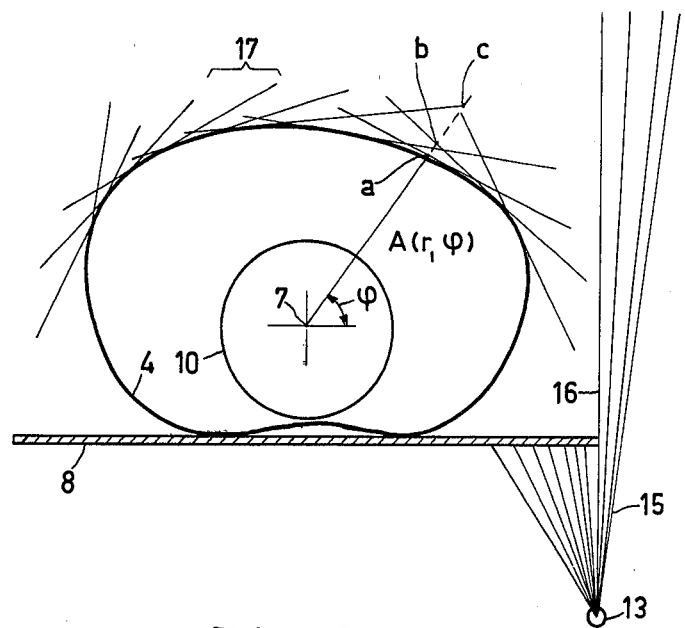
FIG. 2 shows the paths of the auxiliary measuring beams tangent to the body.

FIG. 2 more accurately shows the beam paths of the auxiliary measuring beams 17 tangent to the body 4. The reference numerals 4, 7, 8 and 10 denote the same elements as in FIG. 1. Also shown is a fan of auxiliary measuring beams 15 which originates from the auxiliary radiation source 13 in a given rotary position $\theta$ of the measuring system (detector devices and radiation sources). In this position, an auxiliary measuring beam 16 which is tangent to the examination table 8 is not tangent to the contour of the body 4, so that it should not be used for reconstructing the body contour. The auxiliary measuring beams 17, however, determined from successive measurements at different angles $\theta$ and extending tangentially to the body 4, describe a part of the body contour which is remote from the examination table 8.

An arbitrary vector $A(r, \phi)$ (central vector) which points away from the examination table 8 and which extends at an angle $\phi$ with respect to the X-axis of a system of coordinates X, Y situated in the centre of the examination zone 10, then intersects several auxiliary measuring beams 17 at the points a, b, c . . . . In order to enable determination of a first contour point 18a-c etc. (see FIG. 3), all points of intersection a, b, c . . . of the vector $A(r, \phi)$ with the auxiliary measuring beams 17 are determined, a first contour point being determined on the auxiliary measuring beam which is situated nearest to the centre of the examination zone 10 in accordance with the formula (1):

$$A(r,\phi) = \text{Min}\theta \left\{ \sqrt{X^2(\phi,\theta) + Y^2(\phi,\theta)} \right\} \quad (1)$$

Therein, $X(\phi, \theta)$ and $Y(\phi, \theta)$ are each time the coordinates of the points of intersection a, b, c . . . of the vector $A(r, \phi)$ with the auxiliary measuring beam 17 in the direction $\phi$. These coordinates are determined by means of the formulas $$X(\phi, \theta) = p_t(\theta) \cdot (\sin \theta \cdot \tan \phi + \cos \theta)^{-1} \quad (2)$$

and $$Y(\phi, \theta) = p_t(\theta) \cdot (\sin \theta \cdot \cos \theta \cot \phi)^{-1} \quad (3)$$

Therein, $p_t(\theta)$ is the distance between an auxiliary measuring beam 17 measured by means of the auxiliary detector device 14, 14' and tangent to the body 4 and the centre of the examination zone, the position of which results further from the angular position $\theta$ of the system formed by the radiation source 1 and the radiation detectors 6 and the geometrical arrangement of the auxiliary radiation sources 13, 13' and from the auxiliary detector devices 14, 14'.

Using a large number of vectors $A(r, \phi)$ which all point away from the examination table 8 and wherebetween, for example, an equal selected angular distance $\Delta\phi$ exists, upper first contour points 18a-c . . . etc. (see FIG. 3) can thus at least be approximately determined.

Figure 3:
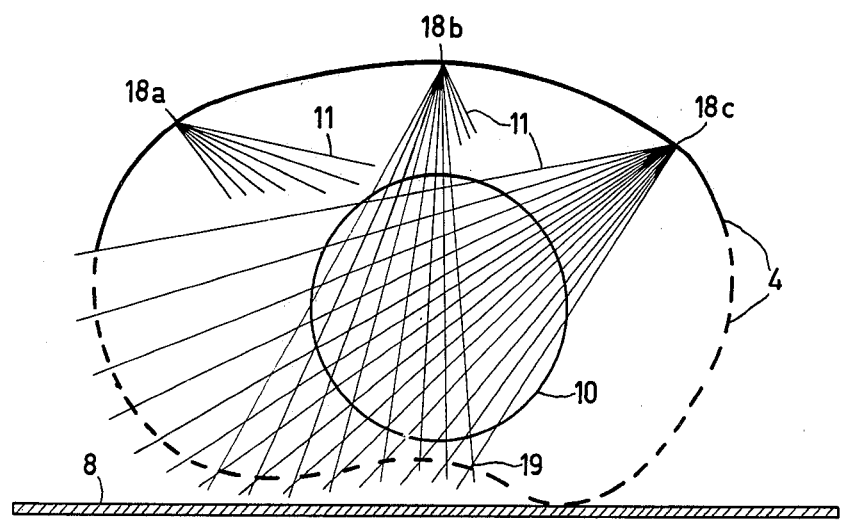
FIG. 3 is a sectional view of the body, positioned in the plane of examination, with beam paths extending through first contour points.

In FIG. 3 it is assumed that the upper contour of the body 4 (non-interrupted line) has already been determined. When the body 4 is irradiated with parallel or fan-shaped measuring beams—both radiation geometries can be converted one into the other in known manner—more than one beam path 11 extends through each first contour point in different directions which are situated in the plane and through the examination zone 10. When, starting from the first contour points 18a-c, a length is plotted in the direction of the body 4 on each beam path 11, said length being determined from the quotient $L(p, \theta) = Q(p, \theta)/\bar{\mu}$, $\bar{\mu}$ being a predetermined mean absorption coefficient which approximates the body absorption coefficient, further contour points 19 are obtained which describe at least approximately the contour of the body 4 facing the examination table 8.

The length of the vectors $A(r, \phi)$ associated with the further contour points 19 is then corrected by a multiplicative factor F so that no tip of any vector projects through the examination table 8. to this end, first other vectors A' are formed in the same directions $\phi$, the lengths $|A'|$ thereof resulting from the distances between the points of intersection of the vectors with the examination table and the centre of the examination zone. The multiplicative factor is then calculated from:

$$F^{-1} = (\text{MAX}_{100}\{|A(r, \phi)/A'(r, \phi)|\} - 1) \cdot |\phi - \phi_o|^{-1} \cdot \Delta\phi + 1$$

when this maximum occurs approximately at the angle $\phi_o$ and $\Delta\phi$ indicates the angular step.

For further increasing the number of contour points of possibly for closing any gaps between the first contour points, on the beam paths 11 extending through the further contour points 19 and the examination zone 10 the quotients $L(p, \theta)$ can be plotted in the described manner, proceeding from the further contour points 19 in the direction of the body 4, in order to obtain additional contour points.

Because the actual absorption along the beam paths 11 can only be approximately represented by the mean absorption coefficients $\bar{\mu}$, the magnitude of the individual vectors $A(r, \phi)$ whose ends represent the contour points are preferably averaged. To this end, vectors are formed which point to the further and possibly also to the additional contour points, the magnitudes of said vectors being averaged each time in small angular zones Δφ in order to obtain corrected contour points.

Figure 4:
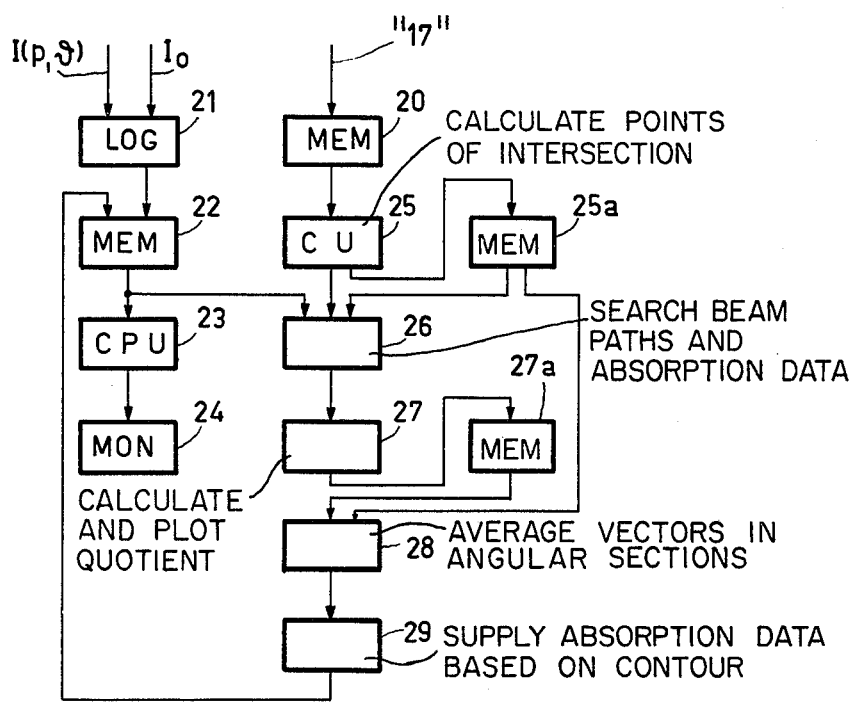
FIG. 4 shows a block diagram of an electronic unit for performing the method.

FIG. 4 shows a block diagram for illustration of the method. The logarithm of the measuring values I(p, θ) (intensities) or the reference intensity $I_o$, measured by means of the detectors 6, is taken in a logarithmation unit 21 which at the same time forms absorption values Q(p, θ) which are stored in a data memory 22. These absorption values are used at a later stage for reconstructing the absorption distribution μ(x, y) in the examination zone 10 in the central computer 23, said distribution being displayed on the monitor 24.

For each of the auxiliary measuring beams 17 which are stored in the memory 20 and which are tangent to the body 4, a first arithmetic unit 25 calculates the points of intersection X(φ, θ), Y(φ, θ) with the paths of each time the central vectors A(r, φ). Customary methods are used for calculating the points of intersection. Subsequently, the unit 25 determines the each time smallest distance between the points of intersection and the centre 7 (FIG. 1) of the examination zone 10, each time along a central vector path A(r, φ). The point of intersection with the smallest distance thus each time forms the end coordinate of a vector or a first contour point 18a, b, c. The measured first contour points 18 are then stored in the intermediate memory 25a. For each of the first contour points 18 stored in the intermediate memory 25a, an arithmetic unit 26 then searches the beam paths 11 extending therethrough and the absorption value Q(p, θ) associated with each beam path 11 and stored in the data memory 22. From each of the absorption values, an arithmetic unit 27 calculates a quotient L(p, θ) which corresponds to a length and plots this length each time on the associated beam path 11 in order to define further contour points 19.

Further central vectors are then formed in the direction of the lower body contour, the ends of said vectors representing the further contour points 19. These further contour points 19 are stored in a further intermediate memory 27a. Also using the first contour points already stored in the memory 25a, the unit 28 shown in FIG. 4 defines corrected contour points representing the body contour points by dividing the total angular zone θ into separate, limited angular sections Δφ and by averaging the value of the vectors A(r, φ) in each angular section Δφ by means of known methods.

On the basis of the defined contour of the body 4, a further arithmetic unit 29 then supplies the absorption data $\overline{Q}$(p, θ) in the described manner, said absorption data also being applied to the data memory 22 for determination of a reconstruction image of the examination zone 10.

What is claimed is:

1. In computed tomography, a method of determining the contour of a body in a plane, said body being positioned on an examination table and further being contained within a positioning zone in the plane, comprising the steps of;
   completely irradiating an examination zone, which is situated within the positioning zone, from a plurality of different directions in the plane of examination with primary radiation which passes through the body along a plurality of beam paths and measuring the radiation transmitted through the body to determine primary radiation absorption values along each of said beam paths;
   irradiating the positioning zone in a region which adjoins the examination zone and is tangent to the perimeter of the positioning zone; from a plurality of directions in the plane with auxiliary radiation which is substantially absorbed by the body;
   measuring the auxiliary radiation with auxiliary detectors to determine the position of auxiliary radiation beams which are tangent to the body;
   determining the position of contour points of the body from the position of said auxiliary radiation beams which are tangent to the body; wherein, as an improvement, the step of determining the position of contour points comprises:
   determining the position of a plurality of first contour points from the position of auxiliary radiation beams which are tangent to the body and do not pass through the examination table;
   determining the position of further contour points by calculating the distance between a further contour point and a first contour point as the quotient of the absorption value determined from the measurement of primary radiation along a beam path which passes through said first point and said further point divided by an assumed value of a mean absorption coefficient in the body.

2. The method of claim 1 wherein the step of determining the position of contour points further comprises determining the position of additional contour points by calculating the distance between an additional contour point and a further contour point as the quotient of the absorption value determined from the measurement of primary radiation along a beam path which passes through said further contour point and said additional contour point divided by the assumed value of the mean absorption coefficient in the body.

3. The method of claim 1 or claim 2 further comprising the step of determining the position of corrected contour points by averaging, in predetermined angular zones, vectors which extend from a center of the examination zone to a plurality of previously determined contour points.

4. The method of claim 1 further comprising the step of calculating an absorption distribution in the body using the measured absorption values along the beam paths and the position of the contour points.

* * * * *